United States Patent

Wolf et al.

[11] Patent Number: 5,965,880
[45] Date of Patent: Oct. 12, 1999

[54] TACTILE OPTO-ELECTRONIC PRESSURE SENSOR

[75] Inventors: Rainer Wolf, Grosswalbur; Lothar Gamer, Bruchsal; Harald Fischer, Karlsruhe, all of Germany

[73] Assignee: Forschungszentrum Karlsruhe GmbH, Karlsruhe, Germany

[21] Appl. No.: 09/019,007

[22] Filed: Feb. 5, 1998

Related U.S. Application Data

[63] Continuation-in-part of application No. PCT/EP96/01810, May 2, 1996.

[30] Foreign Application Priority Data

Jul. 29, 1995 [DE] Germany .......................... 195 27 957

[51] Int. Cl.$^6$ .................................. G01J 1/56; G01J 1/04
[52] U.S. Cl. ............................... 250/231.19; 250/227.14; 901/33
[58] Field of Search ................... 250/231.19, 227.14, 250/229; 73/862.041, 862.046, 705; 901/33, 47

[56] References Cited

U.S. PATENT DOCUMENTS 4,306,148 12/1981 Ringwall et al. .................... 250/229
4,599,908 7/1986 Sheridan et al. ................. 250/227.21

*Primary Examiner*—Edward P. Wastin
*Assistant Examiner*—Kevin Pyo
*Attorney, Agent, or Firm*—Klaus J. Bach

[57] ABSTRACT

In a pressure sensing system comprising a tactile pressure sensor with an opaque cylindrical body disposed in a tube and having axial passages extending between its opposite end faces, an electroluminescent foil is disposed at one end face and a support body which includes light collecting means is disposed at the other end face so that light emitted by the luminescent foil and passing through the passages—dependent on the pressure applied to the one end face—is conducted to an imaging device for determining the pressure distribution applied to the one end face of the cylindrical body.

8 Claims, 2 Drawing Sheets

TACTILE OPTO-ELECTRONIC PRESSURE SENSOR

This is a Continuation-In-Part application of international application PCT/EP96/01810 filed May 2, 1996 and claiming the priority of German Patent application 195 27 957.3 of Jul. 29, 1995.

BACKGROUND OF THE INVENTION

The invention relates to a system including a tactile pressure sensor with an opaque cylindrical body which consists of an elastomer and has several axially extending bores, and an image receiving apparatus with a data processor. The pressure sensor responds to a pressure applied to its tactile part with a light intensity change. This light intensity change is transmitted, by way of a light transmission structure, to an image receiver and is recorded. A data processor connected to the image receiver controls the image receiver and reads the intensity-relevant data. The pressure effective on the pressure sensitive surface can then be displayed or control signals can be transmitted to associated operating equipment or sensing devices.

Such pressure sensors have various applications. They may be used for example as touch-sensitive devices in the robot technology. They can be used for sensing surface conditions. In the medical field, tissue areas or organs can be probed.

A company "Interlink" utilizes a pressure array in a laparoscopic grasping clamp in order to obtain pressure data. The sensor comprises a semi-conductive polymer, which changes its resistance when subjected to external pressure. These pressure data which are suitable only for a dynamic pressure determination are, after a graphic display on a PC monitor, returned to a tactile system (see Fischer, H. et al, "Messungen der Greifkräfte chirurgischer Zangen mit FSRTM-sensors" internal report, Forschungszentrum Karlsruhe, HIT, 1994). The semi-conductive polymer has the disadvantageous property that it ages very rapidly if used frequently, exhibits a very high creep behavior and is therefore not suitable for static pressure measurements since the inference regarding the pressure generated becomes incorrect.

Very common are tactile capacitive foil sensors. They generally consist of two copperstrips which are disposed crosswise on top of each other and are separated by a dielectric elastomer such that they form a condenser matrix (see J. Seekircher et al. "Improved Tactile Sensors", selected papers from the $2^{nd}$ IFAC symposium, Pergamon 1989, p. 317–322). The pressure on the sensor is transformed to a capacity change. However, such an arrangement is very susceptible to electric fields since the signal value is very small because, with a layer thickness of 30 $\mu$m, the capacity changes of 0.6 pF at d/d=10% are very small.

DE 32 36 435 C2 discloses a fiber optic sensor, wherein light is conducted through a tube whose open width is pressure dependent and determines the intensity of light conducted through the tube to a receiver. With such a sensor, however, no layer arrangement can be provided since it is different in principle.

A pressure intensity transmission arrangement, which permits the construction of tactile sensors of small dimensions and with high resolution for the installation into a finger of a robot clamp is described by D. H. Mott et al. FIG. 1 on page 181 shows the principle of the conversion of the pressure intensity into light intensity in ROBOT SENSORS, Volume 2, Tactile and Non-Vision, edited by Prof. A. Pugh, Springer Volag Berlin, Heidelberg, New York, Tokyo, 1986 in the contribution "An Experimental Very High Resolution Tactile Sensor Array", on pages 179 to 188.

The tactile part includes a transparent acrylic plate on which, separated by an air space, a foil in the form of a resilient membrane is disposed. From the side, light is radiated into the acrylic plate, which passes through the plate when there is no load on the plate. The light is reflected on the side walls and exits at the opposite front wall. If the membrane is pressed by outer pressure inputs at any place into contact with the acrylic plate the light reflection in the contact area becomes diffuse because the fraction index changes and light radiates out through the side wall.

The image of the light which is reflected from the tactile sensor in a diffuse manner is directed, by means of optical equipment onto the entrance surface of a CCD chip with a lens disposed in front thereof and is then further processed in a data processor connected to the chip for the display of the video signals or for the generation of control signals for the robot clamp. Also, the CCD camera is controlled and operated by the data processor. Only video images are produced which are generated by a lens system disposed in front. The force applied cannot be determined with this system.

The video images normally produced with CCD chips generally need to be subsequently analyzed by expensive image recognition methods since very large amounts of data are available with for example 486 923 pixels. If PC analyzing units are utilized, the large amount of data which are generated during translation movement in serial cut sections can be used. However, with the hardware utilized in the CCIR standard (international TV standard), there is no data reduction. Such reduction has to be implemented during later processing by expensive software programs. As a video unit the total system is fast but the data processing between the intensity measurement of the light distribution on the CCD chip requires a lot of time. Standard CCD processing provides only visual images without coordination in the form of a voltage signal of the pressure, or respectively, the light intensity effective on the sensor. They serve generally for the visual recognition of objects (textures, outlines).

U.S. Pat. No. 4,599,908 discloses a pressure sensor with a cylindrical body of an elastomer, which includes several axially extending bores. In this sensor, the light is coupled by way of wave guides into the sensor and is reflected at the pressure sensitive end of the sensor in a pressure dependent manner.

It is the object of the present invention to provide a sensor with which static and dynamic pressure distributions on bodies or other objects can be measured in a small surface area in an absolute and dynamic way. A system should be utilized for this purpose comprising a pressure sensor and an imaging device with a data processor. With this system, it should be possible to represent the "finger tip feel" graphically on a monitor. Furthermore, such a system should be suitable for controlling actuators.

SUMMARY OF THE INVENTION

In a pressure sensing system comprising a tactile pressure sensor with an opaque cylindrical body disposed in a tube and having axial passages extending between its opposite end faces, an electroluminescent foil is disposed at one end face and a support body, which includes light collecting means is disposed at the other end face so that light from the luminescent foil passing through the passages—dependent on the pressure applied to the one end face—is conducted to an imaging device for determining the pressure distribution applied to the one end face of the cylindrical body.

In order to be able to handle the flood of data during communication with the CCD chip in an optimal and time saving manner, a signal and data processing system is utilized which includes a double sampling (CDS) stage, an integrator and an A/D converter and furthermore, a microprocessor, which processes the electrical signals which are present in the CCD chip and are location-dependent and proportional to light intensity, by means of a data processor so as to provide a profile representation while a microprocessor times the CCD chip by way of a driver stage with a predetermined frequency.

A loss in physical properties as it occurs with semi-conductive polymers is not to be expected with elastomers, ELs and light wave guides. With the relatively small amount of measuring data provided by the microprocessor by way of the serial intersection, an advance calibration (reference measurement) can be performed when there is no load on the tactile sensors. To this end, the intensity of the light which is generated by the electroluminescent foil and which exits at the other side of the perforated rubber body is measured. As a result, a non-load calibration can take place after each complete relieve of the perforated body, that is, the highest radiation off the light emitting surface is set equal to the zero load of the elastomer cylindrical body. A pressure applied to the side which is covered by the electroluminescent foil in a normal direction reduces the free cross-sections of the bores up to a complete closing of the bores. This represents the highest measurable load on the elastomer. The measuring range can be increased or reduced by the selection of an elastomer with an appropriate module of elasticity.

With the signal and data processing system, the amount of data of the controlling and driving microprocessor is reduced by the factor 817×596=486923 pixels/64 digital measurement values after compilation of the respective lines—as compared with the usual data processing. The numbers given here relate to a particular CCD type. For other applications, another CCD type with more or fewer pixels on the light sensitive entrance surface may be of interest. This is achieved: on one hand by the data reduction via the concept of line integration and, on the other hand, by the software-based compilation of the measurement values to 64 clusters by means of a rapid calculation algorithm in the microprocessor. If only half an image is read, a further data reduction by the factor of 2 can be obtained. The advantage would reside in the reduction of time which would be halved.

The reason herefor is that, in contrast to the video processing of CCD chips, there is no optical object recognition, but only an expression regarding a local pressure distribution by the corresponding locally distributed light intensity. Consequently, only certain pixels, that is, the light-exposed pixels are of interest; those remaining dark are of no interest. Furthermore, the measuring method does not require a lens system, that is, the optical system can be eliminated.

The data gathered in this way can be represented on a monitor in the form of pressure mountains or they can be used for controlling a tactile array which transmits the pressure profile to the finger tips of the operator. With this opto-electronic pressure sensor, the operator feels the object although he does not directly touch it.

The tactile sensor of the opto-electronic sensor according to the invention is particularly advantageous in that the light is emitted from the flexible, electroluminescent foil which is disposed directly on the elastomer material body. The object to be manipulated cannot influence the measurement results by the development of shadows. Also, as a result of its construction, the whole opto-electronic pressure sensor is fully protected from dust and dirt.

An embodiment of the invention will be described below on the basis of the accompanying schematic drawings.

DESCRIPTION OF THE PREFERRED EMBODIMENT

The system described below is designed for use in minimal invasive surgery. The tactile pressure sensor is to be disposed at the end of endoscopically used laparoscopic tweezers for the palpatoric examination of tissue. With today's tweezers, the surgeon has no feel in his fingers since tactile sensory impressions are not noticeably enough transmitted through the mechanical structure of the instrument. He therefore tries to obtain information concerning the tissue under examination by way of the receptors of the joints and muscles. These, however, are more or less position indicators. In addition, there is a visual control. In this regard, the surgeon squeezes the tissue until it becomes white. This, however, represents the upper limit area of the pressure to which tissue can be subjected.

With such a system whose tactile part is installed in the mouth piece of a clamp or tweezer-like instrument, a reproducible calculated measuring unit for directly measuring static and dynamic pressure profiles on a very small surface area is provided. Furthermore, the system permits, at any time, the measuring of absolute pressure.

The distal end of a grasping tweezer for endoscopic applications generally has a diameter of not more than 10 mm.

Figure 1:
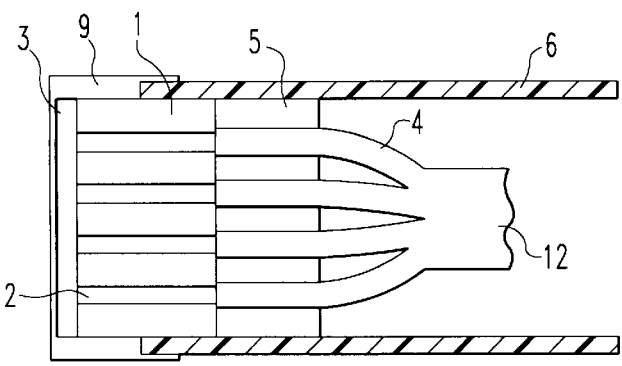
FIG. 1 shows a tactile sensor.
Figure 2A:
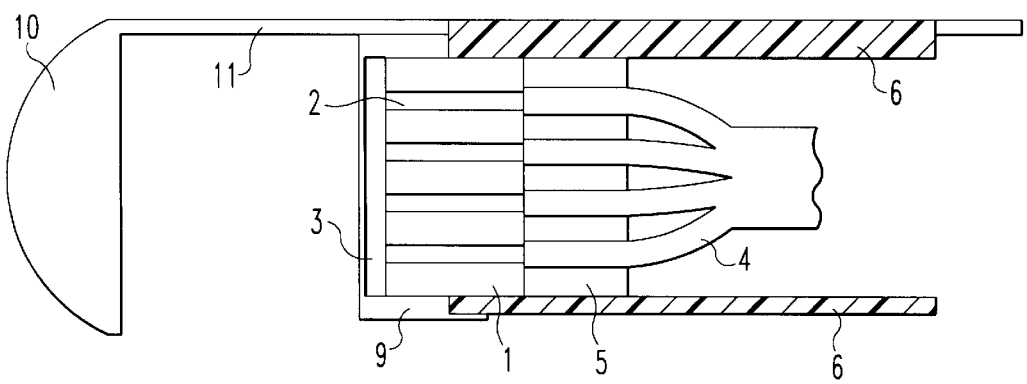
FIGS. 2a and 2b show the tactile sensor installed in a grasping clamp.
Figure 2B:
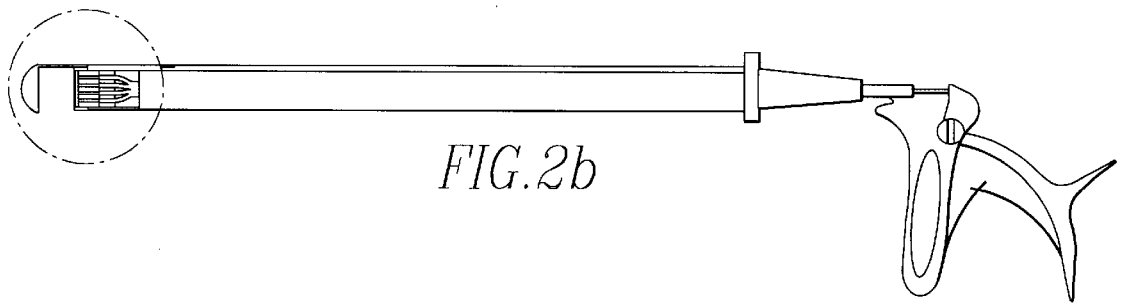

FIG. 1 is a schematic representation of the tactile sensor, FIGS. 2a and 2b show the installation thereof in a grasping tweezer whose movable mouth piece 10 is operable by a pull rod 11 designed for parallel grasping such that pressure can be applied to the tactile part only normal to the surface, that is in the direction of the passages 2. A force limiting structure in the handle of the tweezer provides for a preliminary calibration by assuring always uniform and predetermined compression of the mouth pieces 10.

The tactile part of the pressure sensor consists of a cylindrical opaque elastomer 1 (silicon rubber) with a symmetrical arrangement of 64 passages 2. The passages 2 are all equal and have an open diameter of 0.35 mm each. The passages 2 are collimation passages which permit only light incident normal to the sensor surface to pass. FIGS. 1 and 2a and 2b show only a few passages 2 for simplification.

As shown in FIG. 1, a flexible electroluminescent foil 3 is disposed directly on the front side of the elastomer 1. It has a thickness of 0.17 mm and is covered, together with the free end of the elastomer 1, by a soft envelope 9 consisting of silicon rubber. The electric connections to the foil are not shown in the drawings. Upon application of a voltage, the electroluminescent foil lights up and light passes through the passages 2 and onto light wave guides 4 disposed at the other side of the elastomer 1. Each of the passages 2 receives one light conductor 4, which has a diameter of at least the diameter of the passage 2, but not more than 0.5 mm. The ends of the light conductor 4 are firmly retained in a support body 5 with which they are held in engagement with the elastomer 1 so that the light passing through the passages 2 is directly coupled into the light conductors 4.

If there is no pressure on the elastomer 1, the passages 2 have their largest open width. In this state, the largest amount of light is coupled into the light conductors 4. If the elastomer 1 is subjected to pressure in the predetermined direction—not from the side or at an angle since then the passages 2 would be curved—the diameter of the passages 2 becomes smaller and the intensity of the light exiting the passages becomes less. The elastomer is tightly held in a tubular shaft 6 so that it cannot expand radially outwardly when it is subjected to axial pressure whereby any volume change is compensated for at the expense of the width of the passages 2. The pressure effect can be recorded quantitatively only until the passages 2 are fully closed.

Figure 3:
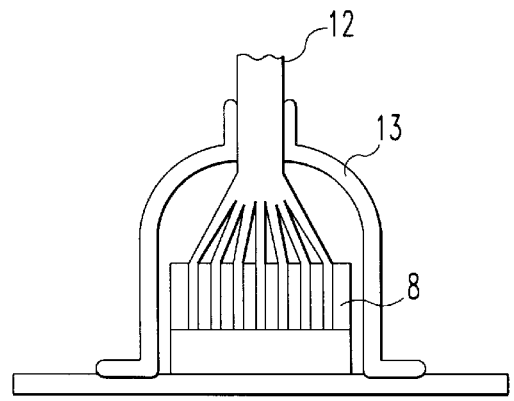
FIG. 3 shows the electro-optical interface.

FIG. 3 shows schematically how the light conductors 4 end on the CCD chip 7: the ends of the light conductors 4 are also mounted in a support body 8 and are disposed directly on the light entrance surface of the CCD chip 7. It is important in this arrangement that the light entrance surface of the bundle 12 of light conductors 4 is similar to the light exit area and the ends are distributed correspondingly such that a local coordination of the light intensity with respect to the effective pressure is established. The opto-electronic interface is protected from outer influences by a hermetically sealed housing 13. The bundle 12 is flexible so that the opto-electronic interface in the form of the CCD chip can be remote from the tweezer or clamp.

Figure 4:
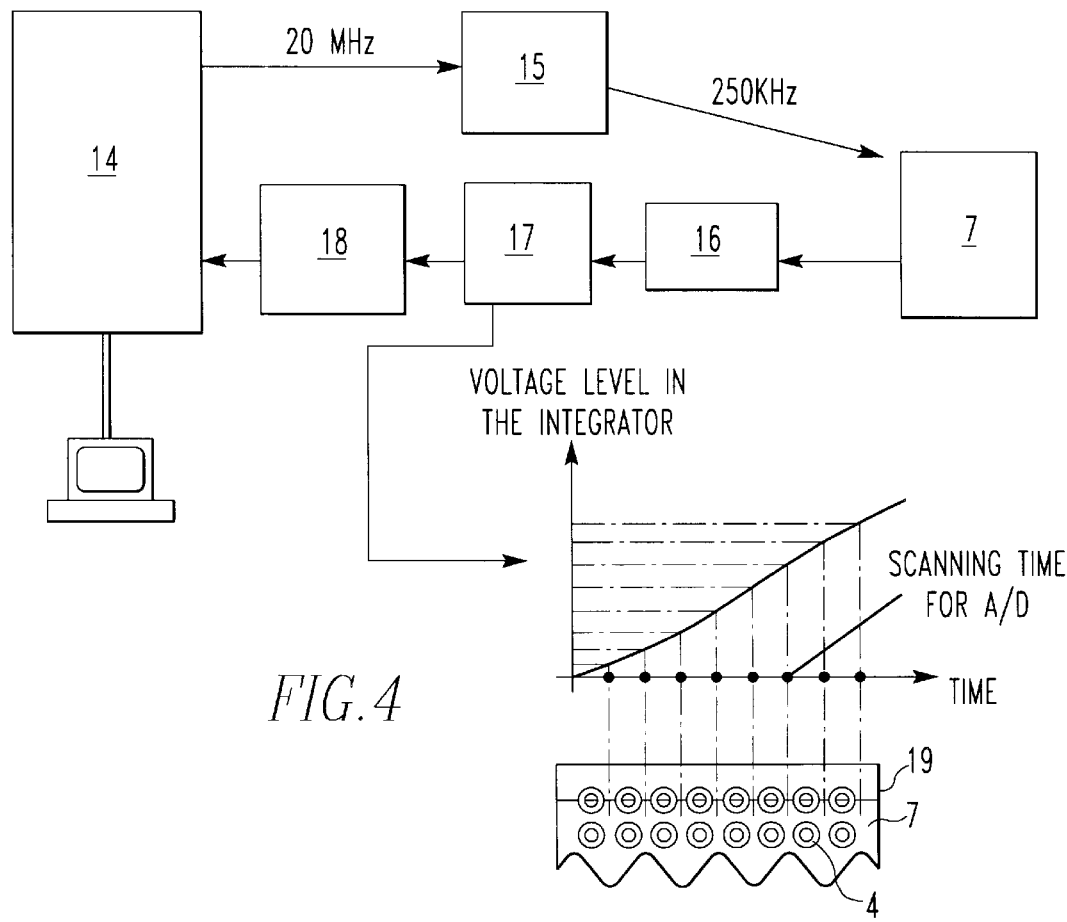
FIG. 4 is a block diagram for signal and data processing.

The CCD-chip is operated in a modified manner (not in accordance with CCIR-international TV standards) as it is shwon schematically in FIG. 4. The evaluation procedure developed for this particular application concerns essentially the data reduction and the processing speed of the signals selected by the CCD chip 7.

The center of the evaluation is a micro-controller 14 which has a maximum pixel frequency of 250 kHz for controlling the CCD chip 7. The timing is software-controlled and consequently very flexible at this point. The tact pulses are converted by the external driver stage 15.

The charge amounts generated in the CCD chip 7 are converted to voltage signals in a subsequent FET voltage stage. These highly temperature-dependent sensor signals are then stabilized by the CDS system 16 in an analog branch. It comprises rapid sample and hold members which are alternatively tacted and which in combination with a differential amplifier filter out noise components. The now stabilized signal voltage is supplied to the integrator 17, which sums up the individual signal voltages of all the pixels of one cell of the CCD chip 7.

The A/D converter 18 scans eight times per line 19. Simply by providing a difference, the values are obtained which correspond to the amount of light fed in through the eight light conductors 4 in each line 19. As a result, a data reduction is achieved from 817 pixel signals to only 8 sum signals per line.

If then all lines 19 are combined which are disposed in the vertical illumination field of a light wave guide 4, after a complete readout of the sensor with its 486923 image points, only the 64 individual measurement values are obtained which corresponds to the surface area integrated amounts of light of the 64 sensor elements.

What is claimed is:

1. A pressure sensor system, comprising a tactile pressure sensor with an opaque cylindrical body consisting of an elastomer material, said cylindrical body having opposite axial end faces and including a plurality of passages extending axially between said end faces, an electroluminescent foil disposed on one of said end faces such that light generated by said electroluminescent foil is directed through said passages, a resilient envelope disposed on said electroluminescent foil such that pressure forces applied to said resilient envelope are transmitted to said cylindrical body, said cylindrical body being closely surrounded by a tube having a portion projecting beyond the other end face of said cylindrical body, and a support body disposed in said projecting tube portion adjacent said cylindrical body, said support body including means for collecting light shining through said passages in said cylindrical body and conducting it to an imaging device which includes an opto-electronic interface.

2. A system according to claim 1, wherein said light conductor consists of one of a rod lens system, a bundle of light conductive fibers, and an image conducting fiber bundle, each having a diameter of at least the diameter of said passages and being disposed in alignment with said passages in said cylindrical body for coupling the light shining through said passages into said light conductive fibers for conduction to said imaging device, said imaging device being CCD chip.

3. A system according to claim 2, wherein said opto-electronic interface comprising the end surfaces of the light conductors and the CCD chips are disposed in an opaque housing.

4. A system according to claim 3, wherein said tactile sensor at the end of said tubular shaft and parts of the light conductors are contained in said tubular shaft such that said pressure sensor can be used as a pressure rod sensor.

5. A system according to claim 4, wherein said pressure sensor is installed in a shaft of a surgical tweezer instrument with an elongated shaft such that the pressure sensitive surface of said cylindrical body extends normal to the shaft of said surgical instrument, said surgical instrument including a movable mouth piece with an engagement surface extending parallel to said pressure sensitive surface and being movable relative thereto so that tissue disposed therebetween can be sensed.

6. A system according to claim 5, further including a data processor including a correlated double sampling (CDS) stage, an integrator and an A/D converter for processing electrical position-dependent, light intensity proportional signals present in the CCD chip by way of a data processor for generating a pressure profile, said microprocessor timing said driver stage of said CCD chip with a predetermined frequency.

7. A system according to claim 6, wherein said driver stage comprises an adapted hardware configuration in ASIC technique (Application Specific Integrated Circuit).

8. A system according to claim 6, wherein said driver stage comprises an adapted hardware configuration in FPGA technique (Field Programmable Gate Array).

* * * * *